United States Patent
Smith

(10) Patent No.: US 12,127,875 B1
(45) Date of Patent: Oct. 29, 2024

(54) MEDITATION AUSCULTATION DEVICE

(71) Applicant: Julian Smith, Miami, FL (US)

(72) Inventor: Julian Smith, Miami, FL (US)

(73) Assignee: INPULSE MEDITATION LLC, Miami, FL (US)

( * ) Notice: Subject to any disclaimer, the term of this patent is extended or adjusted under 35 U.S.C. 154(b) by 448 days.

(21) Appl. No.: 17/167,292

(22) Filed: Feb. 4, 2021

(51) Int. Cl.
*A61B 7/00* (2006.01)
*A61B 7/04* (2006.01)

(52) U.S. Cl.
CPC .............. *A61B 7/003* (2013.01); *A61B 7/04* (2013.01)

(58) Field of Classification Search
CPC .................................. A61B 7/003; A61B 7/04
See application file for complete search history.

(56) References Cited

U.S. PATENT DOCUMENTS

| 10,768,665 | B2 | 9/2020 | Aimone et al. | |
|---|---|---|---|---|
| 2002/0172381 | A1* | 11/2002 | Wang | H04R 1/14 381/190 |
| 2006/0145878 | A1* | 7/2006 | Lehrman | A61B 7/003 340/575 |
| 2006/0239489 | A1* | 10/2006 | Franzen | H04R 5/033 381/375 |
| 2018/0125038 | A1* | 5/2018 | Hord | G08B 15/00 |
| 2019/0069873 | A1* | 3/2019 | Copt | A61B 7/04 |
| 2020/0098345 | A1* | 3/2020 | Loriaux | A61B 7/02 |

* cited by examiner

*Primary Examiner* — Andrey Shostak
(74) *Attorney, Agent, or Firm* — Brent Whitlock Law, LLC; Brent K. Whitlock

(57) ABSTRACT

A meditation auscultation device that can be used to listen to one's heartbeat and breathing during meditation practice is disclosed.

6 Claims, 5 Drawing Sheets

MEDITATION AUSCULTATION DEVICE

CROSS-REFERENCE TO RELATED APPLICATION

Not Applicable.

TECHNICAL FIELD

The present invention relates generally to meditation. More particularly, the present invention concerns a meditation device to aid with yoga, mindfulness, concentration, and relaxation.

BACKGROUND

Regular yoga and meditation practices have been proven to create mental clarity and calmness, increase body awareness, relieve chronic stress, relax the mind, center attention, and sharpen concentration. The daily incorporation of meditation and breathing practices can also improve a person's overall mental well-being. While there are various types of meditation including focused attention, mindful meditation, and open-monitoring meditation, at the center of each meditation practice is breathing. Various studies have shown that there is a biochemical relationship between a person's breathing and their brain. By placing a focus on breathing, an individual has the ability to create an altered state of consciousness.

As yoga and meditation have gained popularity over the years, various attempts have been made to assist or aid individuals in reaching the desired meditative state or state of consciousness. Such attempts include meditation mobile apps, meditation candles, aromatherapy, cranial massages, Zen gardens, "mindfulness chairs", singing bowls, meditative music, and sound recordings. The challenge with the current meditation aids is that their use requires a user to focus on an external stimulant to achieve internal mindfulness. This includes the use of wearable devices.

Attempts have been made, although unsuccessfully, to aid a user with mindfulness. One illustrative attempt can be seen with respect to U.S. Pat. No. 10,768,665 B2, which generally discloses a system and method for enhanced mental training using a virtual reality environment and bio-signal data. While this disclosure does provide a means to reduce stress and focus attention, the disclosure does not permit the use to freely engage in various meditation practices while utilizing the device.

Another attempt can be seen with respect to various breathing tools commercially available on the market that encourage users to push measured breaths into the device in order to gain better control of the user's breathing patterns. While this disclosure provides for a means for the user to control their breathing, it does not encourage the mastery of specific meditation practices or breathing techniques.

As can be seen, various attempts have been made which may be found in the related art but have been unsuccessful. Therefore, a need exists for a new meditation device that allows a user to freely engage in various meditation practices without the input from an external stimulant to avoid the challenges and problems with the prior art.

SUMMARY OF THE INVENTION

It is to be understood that in the present disclosure, all embodiments are provided as illustrative and non-limiting representatives of many possible embodiments. In addition, the terms "is," "can," "will," and the like are herein used as synonyms for and interchangeable with terms such as "may," "may provide for," and "it is contemplated that the present invention may" and so forth.

Furthermore, all elements listed by name, such as yoga, meditation, breathing, concentration, etc., are herein meant to include or encompass all equivalents for such elements. For example, in addition to a "auscultation", any device that permits a user to listen to the user's own heartbeat and breathing is also contemplated by the present invention. In addition to a "choker" any neckcloth or high collar that fits snugly around the neck is also contemplated by the present invention. Such equivalents are contemplated for each element named in its particular herein. Also, while the invention will be described in connection with meditation practices, it is understood that the invention is not limited in scope to use with meditation practices.

For purposes of summarizing, certain aspects, advantages, and novel features of the present invention are provided herein. It is to be understood that not all such aspects, advantages, or novel features may be provided in any one particular embodiment. Thus, the disclosed subject matter may be embodied or carried out in a manner that achieves or optimizes one aspect, advantage, or novel feature or group of features without achieving all aspects, advantages, or novel features as may be taught or suggested.

In view of the foregoing disadvantages inherent in the known art, the present invention provides a novel solution for a meditation auscultation device that can be worn to monitor, stabilize, and enhance a user's meditative breathing techniques while simultaneously allowing the user to engage in a deeper meditative state.

The features of the invention which are believed to be novel are particularly pointed out and distinctly claimed in the concluding portion of the specification. These and other features, aspects, and advantages of the present invention will become better understood with reference to the following drawings and detailed description.

In some embodiments, the present invention may provide for an auscultation member removably attached to the front of a neck collar. The auscultation member further comprises of a diaphragm, an acoustic chamber, and hollow acoustic tubes that are configured to allow sound to travel through the tubes to the ear buds.

The present invention's configuration allows for the diaphragm of the auscultation member to rest on the user's suprasternal notch (i.e. jugular notch), between the user's clavicles and above the manubrium of the sternum. In a preferred embodiment of the present invention, and while in use, the meditation auscultation device is worn snuggly around the neck of a user while the ear buds are placed in the user's ears. During meditation practice, the present invention allows the user to listen to the user's own breathing and heartbeat, thereby allowing the user to reach a desired meditative state or state of consciousness.

In some embodiments, the present invention may be configured to have an adjustable neck collar for use by users having different neck widths. In other embodiments, the present invention may provide for adjustable acoustic tubes so that users may adjust the hollow acoustic tubes to their preferred height.

The embodiments of the invention described herein are exemplary and numerous modifications, variations and rearrangements can be readily envisioned to achieve substantially equivalent results, all of which are intended to be embraced within the spirit and scope of the invention. Furthermore, while the preferred embodiment of the invention has been described in terms of the components and configurations, it is understood that the invention is not intended to be limited to those specific dimensions or configurations but is to be accorded the full breadth and scope of the spirit of the invention.

BRIEF DESCRIPTION OF THE DRAWINGS

These and other features, aspects and advantages of the present invention will become better understood with regard to the following description, appended claims, and accompanying figures where:

DETAILED DESCRIPTION

The present invention overcomes the limitations of the prior art by providing a new and more effective meditation auscultation device and method of using the same.

All dimensions specified in this disclosure are by way of example only and are not intended to be limiting. Further, the proportions shown in these Figures are not necessarily to scale. As will be understood by those with skill in the art with reference to this disclosure, the actual dimensions and proportions of any embodiment or element of an embodiment disclosed in this disclosure will be determined by its intended use.

It is to be understood that the drawings and the associated descriptions are provided to illustrate potential embodiments of the invention and not to limit the scope of the invention. Reference in the specification to "one embodiment" or "an embodiment" is intended to indicate that a particular feature, structure, or characteristic described in connection with the embodiment is included in at least an embodiment of the invention. The appearances of the phrase "in one embodiment" or "an embodiment" in various places in the specification are not necessarily all referring to the same embodiment.

Throughout the drawings, reference numbers are re-used to indicate correspondence between referenced elements. In addition, the first digit of each reference number indicates the figure where the element first appears.

As used in this disclosure, except where the context requires otherwise, the term "comprise" and variations of the term, such as "comprising", "comprises" and "comprised" are not intended to exclude other additives, components, integers or steps.

In the following description, specific details are given to provide a thorough understanding of the embodiments. However, it will be understood by one of ordinary skill in the art that the embodiments may be practiced without these specific details. Well-known features, elements or techniques may not be shown in detail in order not to obscure the embodiments.

Figure 1:
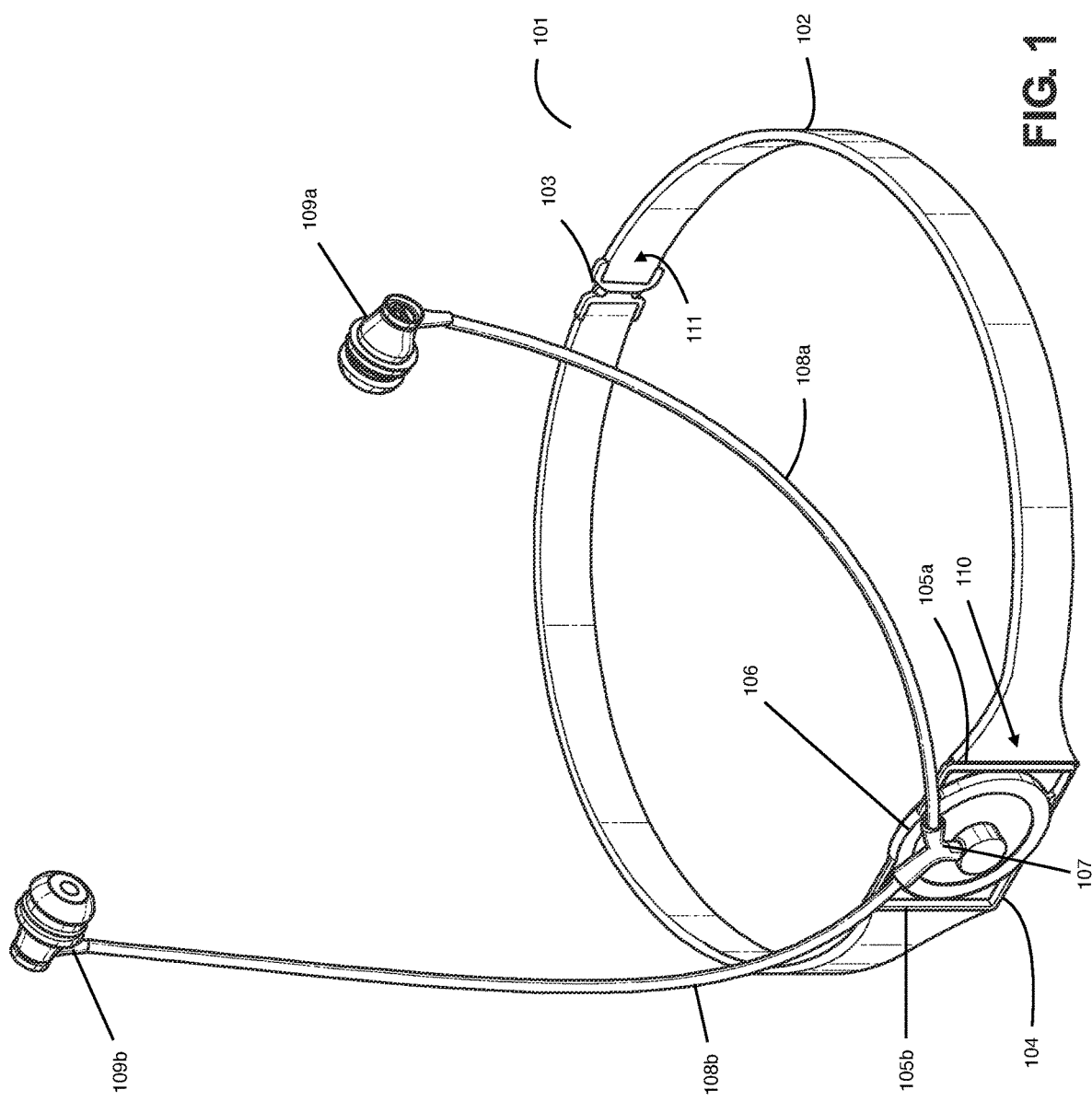
FIG. 1 shows a perspective view of a meditation auscultation device in accordance with an embodiment of the invention.

Turning attention to FIG. 1, a perspective view of a meditation auscultation device in accordance with an embodiment of the invention is shown. In the embodiment depicted, a viewer may perceive a meditation auscultation device 101, a neck collar 102, a collar clasp 103, a auscultation frame 104 that is removably connected to the neck collar 102 via the auscultation frame's 104 right-side member 105a and a left side member 105b. In the embodiment shown, the auscultation frame 104 that contains an auscultation chamber 106, and a split sound conduit 107 allowing the sound to be transported from the auscultation chamber 106 through hollow acoustic tubes 108a, 108b that extend from the split sound conduit 107 which hollow acoustic tubes 108a, 108b are configured to deliver the auscultation sound to the headphones 109a, 109b that is auscultated by the auscultation chamber 106. A viewer may also perceive that the neck collar 102 has a proximal end 110 affixed to the right-side member 105a and left-side member 105b of the auscultation frame 104 and a distal end 111 affixed to the collar clasp 103.

Figure 2:
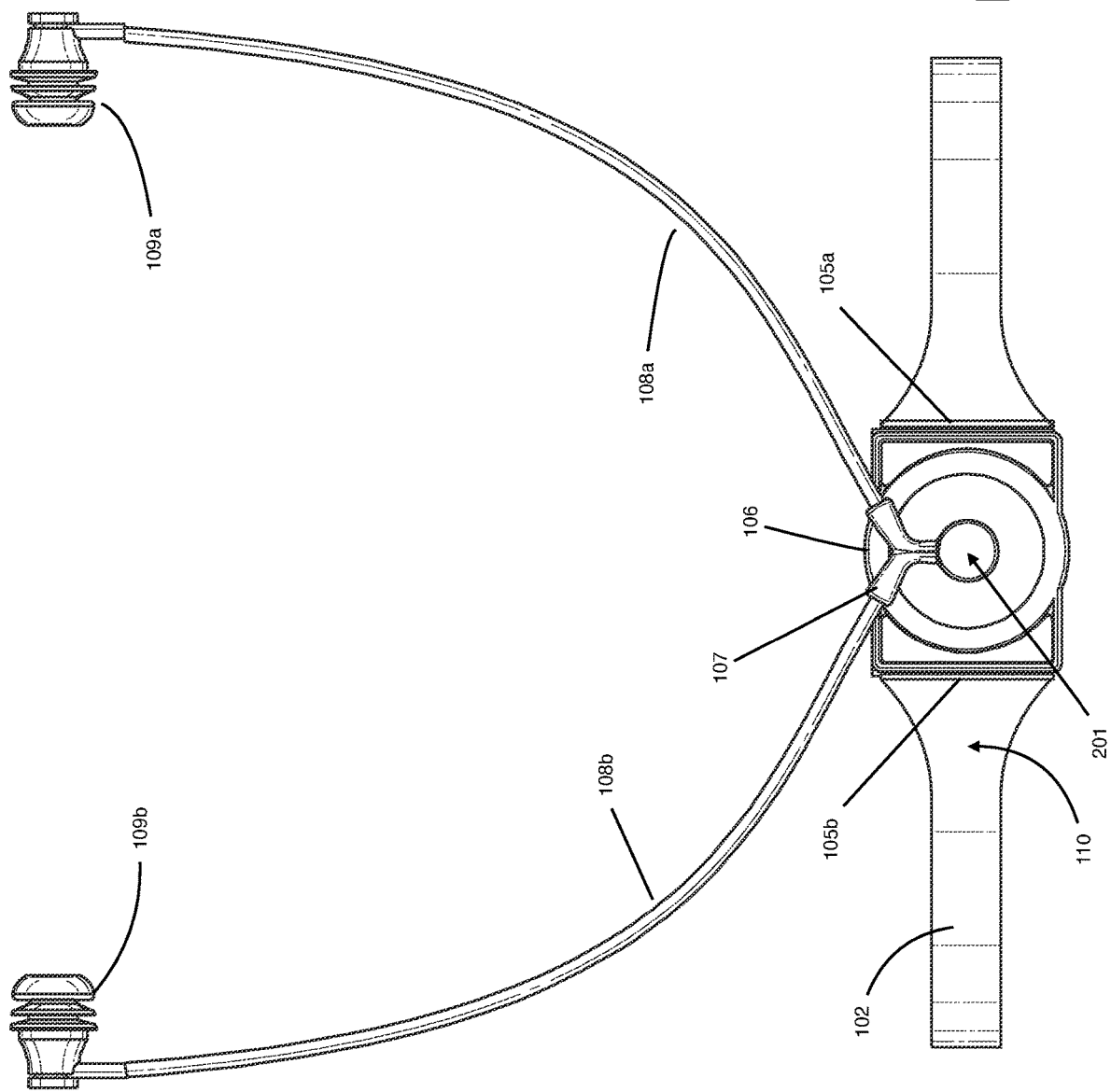
FIG. 2 shows a front view of a meditation auscultation device in accordance with an embodiment of the invention.

With respect to FIG. 2, a front view of a meditation auscultation device in accordance with an embodiment of the invention may be perceived. In the embodiment depicted, a viewer may perceive that split sound conduit 107 allows for the hollow acoustic tubes 108a, 108b to connect to the auscultation chamber 106 by means of the sound conductor 201.

Figure 3:
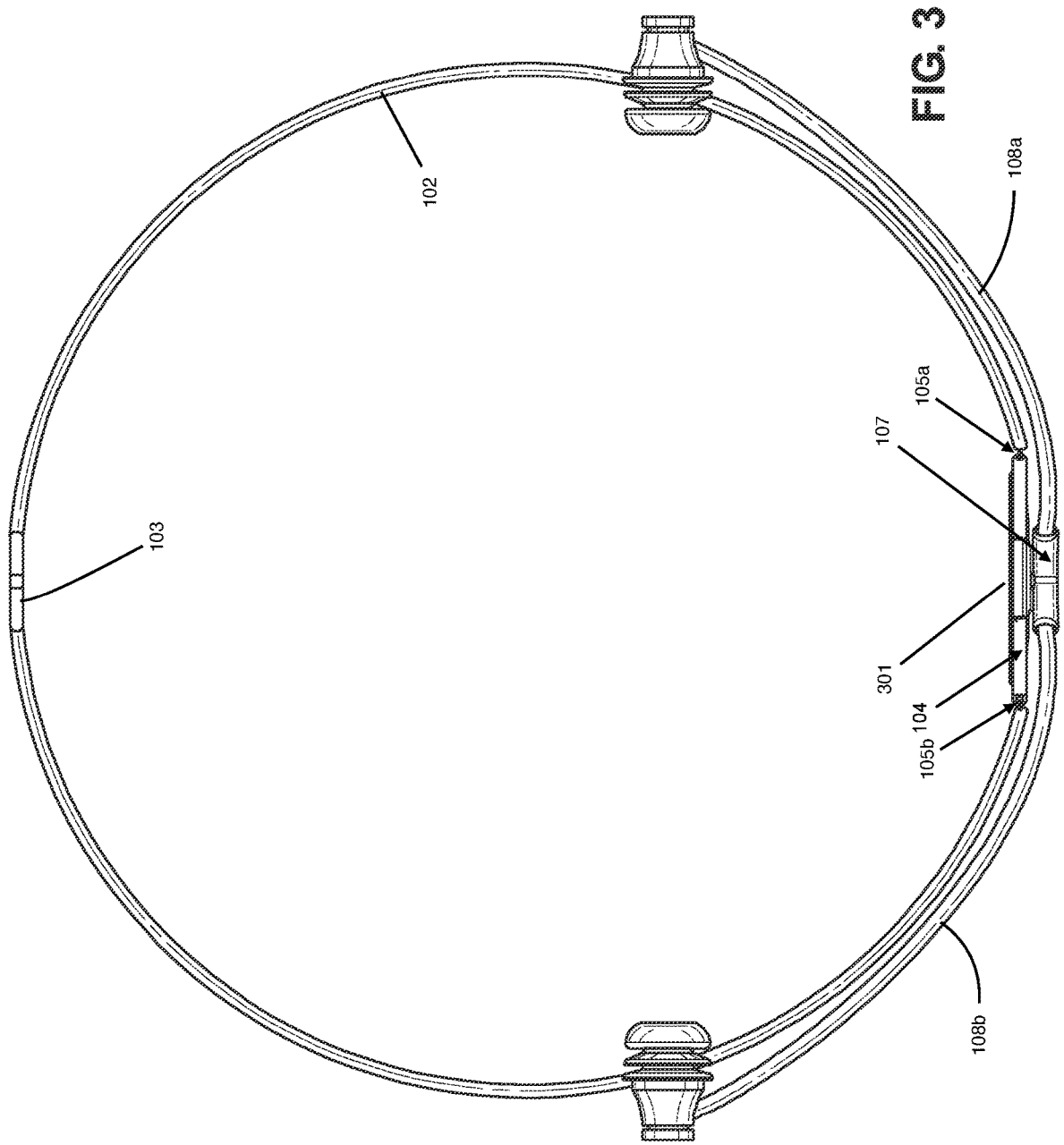
FIG. 3 shows a top view of a meditation auscultation device in accordance with an embodiment of the invention.

With respect to FIG. 3, and as may be generally known in the art, the auscultation frame 104 has a flat rear facing diaphragm 301 that is configured to rest on the user's suprasternal notch while the meditation auscultation device is in use. A viewer may perceive that the acoustic chamber 107 and headphone cords 108a, 108b extend away from the front surface of the frame 104.

Figure 4:
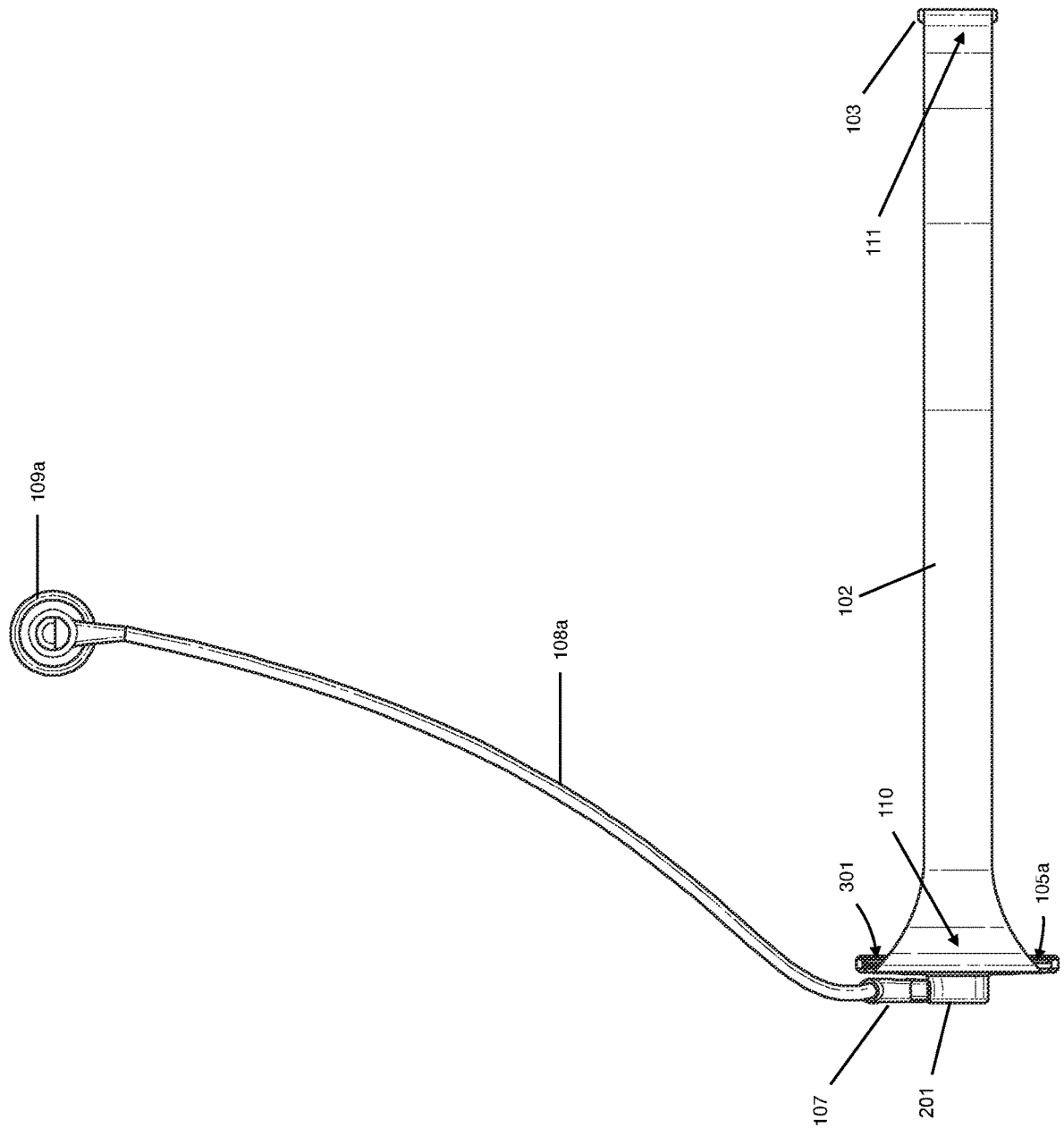
FIG. 4 shows a right view of a meditation auscultation device in accordance with an embodiment of the invention.

As may be seen in FIG. 4, a side view of a meditation auscultation device in accordance with an embodiment of the invention may be seen. In the embodiment shown, a viewer may perceive that the sound conductor 201 extends from the front surface of the auscultation chamber 106 (not shown) at a 90-degree angle. A viewer may also perceive that the split sound conduit 107 is fixedly connected to the top of the auscultation chamber 106.

Figure 5:
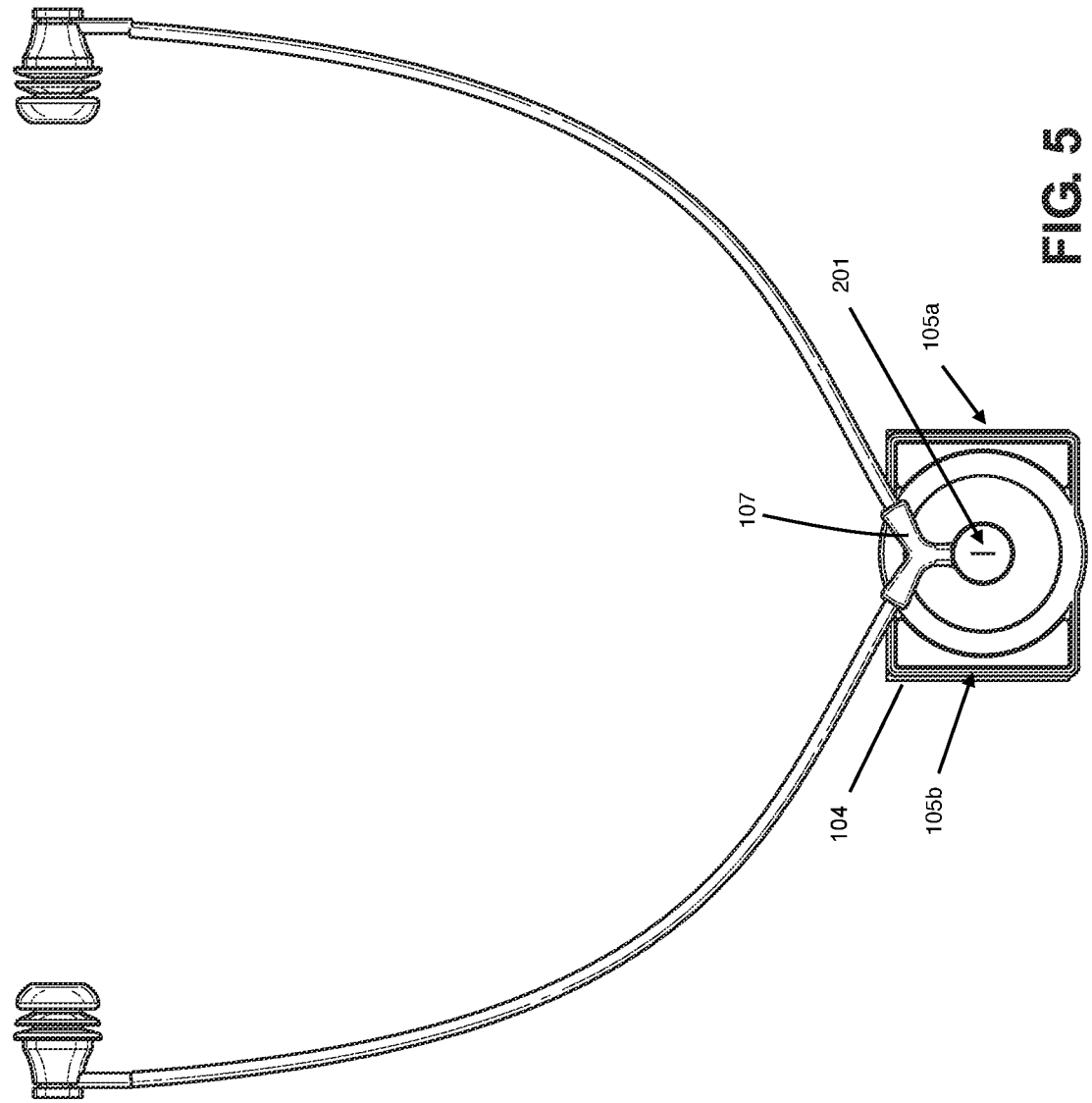
FIG. 5 shows a front view of a meditation auscultation device in accordance with an alternative embodiment of the invention.

Turning attention to FIG. 5, a front view of a meditation auscultation device in accordance with an alternative embodiment of the invention is shown. In the embodiment shown, a viewer may perceive that the proximal end 110 of the neck collar 102 has been removed from the auscultation frame's 104 side members 105a, 105b.

CONCLUSIONS, RAMIFICATIONS, AND SCOPE

Although the present invention has been described with a degree of particularity, it is understood that the present disclosure has been made by way of example and that other versions are possible. As various changes could be made in the above description without departing from the scope of the invention, it is intended that all matter contained in the above description or shown in the accompanying drawings shall be illustrative and not used in a limiting sense. The spirit and scope of the appended claims should not be limited to the description of the preferred versions contained in this disclosure.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function should not be interpreted as a "means" or "step" clause as specified in 35 U.S.C. § 112.

While the present invention generally described herein has been disclosed in connection with a number of embodiments shown and described in detail, various modifications should be readily apparent to those of skill in the art.

What is claimed is:

1. A meditation auscultation device comprising:
    an auscultation frame comprising a diaphragm, an auscultation chamber, a split sound conduit, and a sound conductor, the auscultation frame configured for acoustically monitoring a user's auscultation sounds;
    an adjustable neck collar removably attached to the auscultation frame and configured to adjustably position the diaphragm to rest on the user's suprasternal notch while acoustically monitoring the user's auscultation sounds;
    at least one adjustable hollow acoustic tube extending from the sound conductor and configured to acoustically propagate the user's auscultation sounds; and
    at least one earbud fixedly connected to the at least one adjustable hollow acoustic tube and configured to acoustically propagate the user's auscultation sounds from the at least one adjustable hollow acoustic tube to the user's respective ear.

2. The meditation auscultation device of claim 1 wherein the adjustable neck collar comprises a right-side member and a left-side member, a proximal end of the right-side member is configured to removably attach to a right side of the auscultation frame, and a proximal end of the left-side member is configured to attach to the left side of the auscultation frame.

3. The meditation auscultation device of claim 2 wherein a distal end of the right-side member and a distal end of the left-side member of the adjustable neck collar are removably coupled via a clasp.

4. A meditation auscultation device comprising:
    a diaphragm configured to contact a user's neck for acoustically monitoring the user's breathing and/or heartbeat while meditating;
    an auscultation chamber configured to auscultate auscultation sound in conjunction with the diaphragm;
    an adjustable hollow acoustic tube comprising a proximal end and a distal end, the adjustable hollow acoustic tube operably coupled with the auscultation chamber and configured to acoustically transport the auscultation sound from the proximal end to the distal end for listening by the user while meditating;
    an ear bud operatively coupled with the distal end of the adjustable hollow acoustic tube to acoustically transport the auscultation sound to an ear of the user for the user to listen to the user's own breathing and/or heartbeat while meditating;
    a neck collar, wherein the neck collar is adjustable for adjustably positioning the diaphragm in contact with the user's suprasternal notch, and configured to facilitate selectively positioning the neck collar around the user's neck and removing the neck collar from around the user's neck to selectively listen to the user's auscultation sound; and
    an auscultation frame configured to be attached to the neck collar and configured to adjustably position the diaphragm in contact with the user's suprasternal notch when the neck collar is positioned around the user's neck for acoustically monitoring the user's breathing and/or heartbeat while meditating.

5. The meditation auscultation device of claim 4, wherein the auscultation sound comprises breathing.

6. The meditation auscultation device of claim 4, wherein the auscultation sound comprises a heartbeat.

\* \* \* \* \*